United States Patent
Lo et al.

(10) Patent No.: US 10,909,773 B2
(45) Date of Patent: Feb. 2, 2021

(54) MEDICAL IMAGE MODELING SYSTEM AND MEDICAL IMAGE MODELING METHOD

(71) Applicant: Metal Industries Research & Development Centre, Kaohsiung (TW)

(72) Inventors: Kai-Szu Lo, Tainan (TW); Jian-Jia Tzeng, Kaohsiung (TW); Sheng-Hong Yang, Kaohsiung (TW); Bo-Wei Pan, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 0 days.

(21) Appl. No.: 16/207,198

(22) Filed: Dec. 3, 2018

(65) Prior Publication Data
US 2020/0175774 A1 Jun. 4, 2020

(51) Int. Cl.
*G06T 19/20* (2011.01)
*G06T 17/00* (2006.01)
(Continued)

(52) U.S. Cl.
CPC ............ *G06T 19/20* (2013.01); *G06F 3/0482* (2013.01); *G06F 3/04817* (2013.01); *G06T 7/60* (2013.01);
(Continued)

(58) Field of Classification Search
CPC ........... G06T 19/20; G06T 17/00; G06T 7/60; G06T 2207/30008; G06T 2207/20092;
(Continued)

(56) References Cited

U.S. PATENT DOCUMENTS

| 2007/0132757 A1* | 6/2007 | Hassner | G06T 17/20 345/420 |
| 2008/0085489 A1* | 4/2008 | Schmitt | A61C 1/084 433/75 |

(Continued)

FOREIGN PATENT DOCUMENTS

| CN | 1609899 | 4/2005 |
| CN | 103919631 | 7/2014 |

(Continued)

OTHER PUBLICATIONS

"Office Action of Taiwan Counterpart Application", dated Aug. 20, 2019, p. 1-p. 5.

*Primary Examiner* — Sae Won Yoon
(74) *Attorney, Agent, or Firm* — JCIPRNET (57) ABSTRACT

A medical image modeling system and a medical image modeling method are provided. The medical image modeling system includes an input device, a processing device, and a storage device. The input device obtains medical image data. The processing device is coupled to the input device. The processing device converts the medical image data into a bone model in response to a first operational command. The storage device is coupled to the processing device. The storage device stores a model database. The processing device reads the model database in response to a second operational command to obtain a bone reconstruction block corresponding to a defect block of the bone model. The processing device integrates a bone reconstruction model depicted corresponding to the bone reconstruction block into the defect block of the bone model to generate an integrated bone model.

10 Claims, 5 Drawing Sheets

(51) Int. Cl.
*G06T 7/60* (2017.01)
*G06F 3/0481* (2013.01)
*G16H 30/40* (2018.01)
*G06F 3/0482* (2013.01)

(52) U.S. Cl.
CPC .............. *G06T 17/00* (2013.01); *G16H 30/40* (2018.01); *G06T 2200/24* (2013.01); *G06T 2207/20092* (2013.01); *G06T 2207/30008* (2013.01); *G06T 2219/2004* (2013.01)

(58) Field of Classification Search
CPC ......... G06T 2200/24; G06T 2219/2004; G06T 5/005; G06T 7/0012; G06T 2200/04; G06T 2007/10081; G06T 2207/10088; G06T 2207/30036; G06T 2207/30052; G16H 30/40; G16H 20/40; G16H 50/50; G06F 3/04817; G06F 3/0482; G06F 3/04815
USPC ......................................................... 345/420
See application file for complete search history.

(56) References Cited

U.S. PATENT DOCUMENTS

| | | | | |
|---|---|---|---|---|
| 2012/0015316 | A1* | 1/2012 | Sachdeva | G06T 17/00 433/24 |
| 2013/0110469 | A1* | 5/2013 | Kopelman | A61B 5/0088 703/1 |
| 2015/0025855 | A1* | 1/2015 | Fisker | A61C 8/0077 703/1 |
| 2015/0051650 | A1* | 2/2015 | Verstreken | G06F 19/00 606/281 |
| 2017/0172713 | A1* | 6/2017 | Alvarez | A61C 8/0001 |
| 2018/0147015 | A1* | 5/2018 | She | G06T 5/002 |
| 2018/0318011 | A1* | 11/2018 | Leibinger | A61F 2/30942 |
| 2020/0166907 | A1* | 5/2020 | Frederick | B33Y 50/00 |

FOREIGN PATENT DOCUMENTS

| | | |
|---|---|---|
| CN | 105405167 | 3/2016 |
| CN | 104736044 | 11/2017 |
| TW | 200843689 | 11/2008 |
| TW | 201738849 | 11/2017 |

* cited by examiner

MEDICAL IMAGE MODELING SYSTEM AND MEDICAL IMAGE MODELING METHOD

TECHNICAL FIELD

The invention relates to an image modeling technique. More particularly, the invention relates to a medical image modeling system and a medical image modeling method.

DESCRIPTION OF RELATED ART

In the treatment for bone repair, it is common to use an artificial bone repair model to restore bone defects in bone repair surgery. Common oral bone defects are caused by car accident injuries, infection, and cancer and tumor most of the time. The patient may experience face deformation or even loses the ability to speak, chew or swallow, and oral function, appearance, and mental health of the patient may be seriously affected as well. Nevertheless, the conventional artificial bone repair model is made by using medical image software to read a medical image of the bone tissue and then using conversion software to convert the medical image into a stereoscopic bone image. For this reason, production of the conventional artificial bone repair model involves a complex process of image file format conversion, which is rather inconvenient for producing the repair model. Therefore, how to provide a fast and convenient modeling system is an important issue, and several solutions and implementations are thus provided as follows.

SUMMARY

The invention provides a medical image modeling system and a medical image modeling method capable of rapidly and conveniently performing bone model editing and providing a favorable bone reconstruction model editing effect.

The medical image modeling system of this invention includes an input device, a processing device, and a storage device. The input device is configured to obtain medical image data. The processing device is coupled to the input device. The processing device is configured to convert the medical image data into a bone model in response to a first operational command. The storage device is coupled to the processing device. The storage device is configured to store a model database. The processing device reads the model database in response to a second operational command to obtain a bone reconstruction block corresponding to a defect block of the bone model. The processing device integrates a bone reconstruction model depicted corresponding to the bone reconstruction block into the defect block of the bone model to generate an integrated bone model.

In an embodiment of the invention, the medical image modeling system further includes a display device. The display device is configured to display an operation interface. The processing device simultaneously displays a medical image and a bone model image in a window in the operation interface according to the medical image data and the bone model.

In an embodiment of the invention, the processing device edits an area of the bone reconstruction block in the window in the operation interface in response to a third operational command.

In an embodiment of the invention, the storage device further stores a model editing module. The processing device executes the model editing module in response to a fourth operational command, so as to perform a model editing operation within the area of the bone reconstruction block on the bone model through an editing function provided by the model editing module to depict and edit the bone reconstruction model or a surgical guide plate model.

In an embodiment of the invention, the processing device outputs the edited bone reconstruction model to an output device according to a specific data format so that the output device performs model manufacturing.

In an embodiment of the invention, the storage device further stores an image processing module. The processing device executes the image processing module in response to the first operational command to execute an image processing operation on the medical image data. The image processing operation includes bone density, size, and angle measurement, layer-slicing browsing, or pixel data extraction operation.

In an embodiment of the invention, the bone model includes a plurality of classification icons. The processing device selects at least one of the classification icons of the bone model in response to a fifth operational command. The processing device correspondingly reads the model database according to a selection result of the classification icons to obtain the bone reconstruction block.

In an embodiment of the invention, the bone model is a mandible model.

The medical image modeling method of this invention further includes the following steps. Medical image data is obtained. The medical image data is converted into a bone model in response to a first operational command. The model database is read in response to a second operational command to obtain a bone reconstruction model corresponding to a defect block of the bone model. The bone reconstruction model depicted corresponding to the bone reconstruction block is integrated into the defect block of the bone model to generate an integrated bone model.

In an embodiment of the invention, the medical image modeling method further includes the following steps. An operation interface is displayed and a medical image and a bone model image are simultaneously displayed in a window in the operation interface according to the medical image data and the bone model.

In an embodiment of the invention, the medical image modeling method further includes the following steps. An area of the bone reconstruction block in the window in the operation interface is edited in response to a third operational command.

In an embodiment of the invention, the medical image modeling method further includes the following steps. The model editing module is executed in response to a fourth operational command to perform a model editing operation within the area of the bone reconstruction block on the bone model through an editing function provided by the model editing module.

In an embodiment of the invention, the medical image modeling method further includes the following steps. The edited bone reconstruction model is outputted to an output device according to a specific data format so that the output device performs model manufacturing.

In an embodiment of the invention, the step of converting the medical image data into the bone model in response to the first operational command includes the following step. The image processing module is executed in response to the first operational command to execute an image processing operation on the medical image data. The image processing operation includes bone density, size, and angle measurement, layer-slicing browsing, or pixel data extraction operation.

In an embodiment of the invention, the step of reading the model database in response to the second operational command to obtain the bone reconstruction block corresponding to the bone model includes the following. At least one of a plurality of classification icons of the bone model is selected in response to a fifth operational command and the model database is correspondingly read according to a selection result of the classification icons to obtain the bone reconstruction block.

In an embodiment of the invention, the bone model is a mandible model.

To sum up, in the medical image modeling system and the medical image modeling method described in the embodiments of the invention, the bone reconstruction block may be rapidly introduced into the bone model through the model database pre-established in the storage device, so that the surgical guide plate model or the bone reconstruction model may be further edited or depicted. Therefore, by the embodiments of the invention, the medical image modeling system and the medical image modeling method may provide an effective and rapid bone model modeling function.

To make the aforementioned more comprehensible, several embodiments accompanied with drawings are described in detail as follows.

DESCRIPTION OF THE EMBODIMENTS

The term "couple" used throughout this specification (including the claims) may refer to any direct or indirect connection means. For example, if it is described that the first device is coupled to the second device, it should be understood that the first device may be directly connected to the second device or indirectly connected to the second device through other devices, wires, or certain connection means. Moreover, elements/components/steps with the same reference numerals represent the same or similar parts in the figures and embodiments where appropriate. Descriptions of the elements/components/steps with the same reference numerals or terms in different embodiments may be references for one another.

Figure 1:
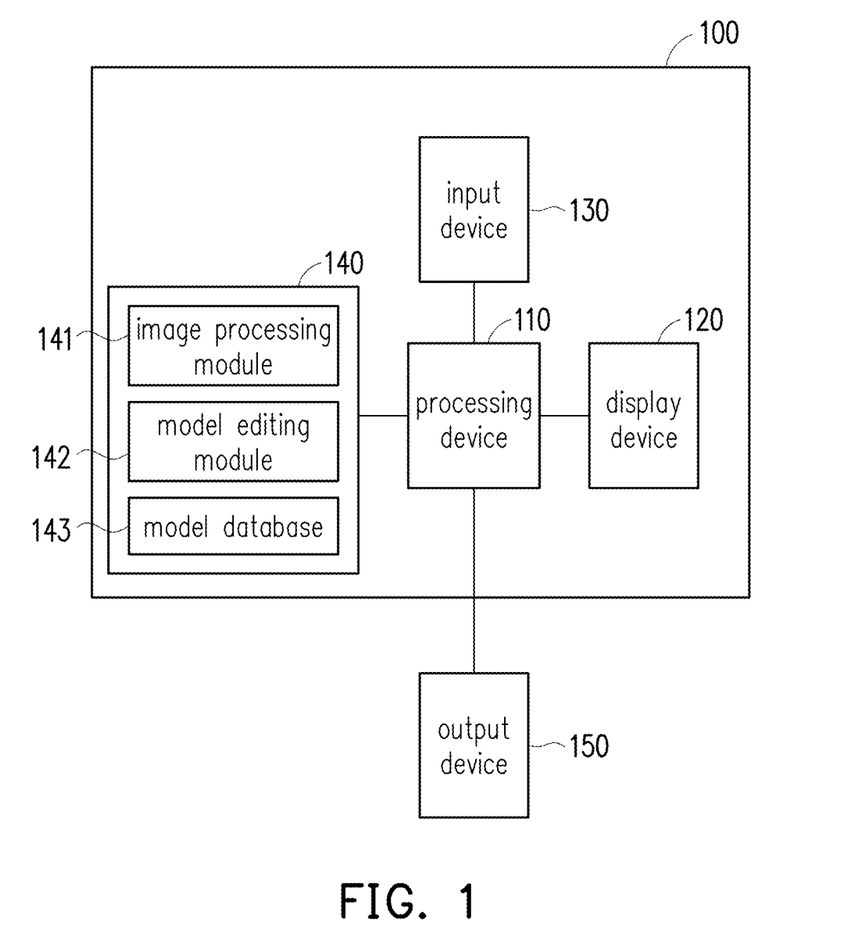
FIG. 1 is a schematic block view of a medical image modeling system according to an embodiment of the invention.

FIG. 1 is a schematic view of a medical image modeling system according to an embodiment of the invention. With reference to FIG. 1, a medical image modeling system 100 includes a processing device 110, a display device, 120, an input device 130, and a storage device 140. The processing device 110 is coupled to the display device 120, the input device 130, and the storage device 140. The processing device 110 may be externally coupled to an output device 150. The storage device 140 may be configured to store an image processing module 141, a model editing module 142, and a model database 143. In this embodiment, the medical image modeling system 100 may read or scan medical image data through the input device 130 and may perform model editing after converting the medical image data into a bone model. Incidentally, the medical image modeling system 100 of this embodiment may be installed in, for example, a workstation, a server or a personal computer (PC), a special medical device, and so on, which is not limited by the invention in this regard.

In this embodiment, the display device 120 is configured to display an operation interface, and the processing device 110 may simultaneously display a medical image and a bone model image in a window in the operation interface according to the medical image data and the bone model, where a bone model presented by the bone model image is a three-dimensional (3D) model. In this embodiment, a user may input an operational command to the medical image modeling system 100 to perform related editing operation and outputs an editing result to the output device 150. Therefore, the medical image modeling system 100 of this embodiment can provide a convenient modeling operation. In addition, other operational commands described in each of the embodiments of the invention may be, for example, a control command, a selection command, a touch command, or an input command and the like generated through, for example, a mouse, a keyboard, a joystick, or other interface devices, which is not limited by the invention in this regard.

In this embodiment, the processing device 110 may be, for example, a central processing unit (CPU) composed of single-core or multi-core or an integrated circuit (IC) for a general purpose or a special purpose, a microprocessor, an image signal processor (ISP), a digital signal processor (DSP), a programmable controller, an application specific integrated circuit (ASIC), a programmable logic device (PLD) or other similar devices, or a combination of the above devices for executing an operational command, an arithmetic instruction, or an algorithm related to the image processing module 141, the model editing module 142, and the model database 143 of the embodiments of the invention.

In this embodiment, the input device 130 may be, for example, a keyboard, a scanner, a card reader, a magnetic disk, a flash drive, or a CD player and the like, and the invention is not limited thereto. In this embodiment, the storage device 140 may be a random access memory (RAM), a read-only memory (ROM), or a flash memory and the like, and the invention is not limited thereto. The storage device 140 may at least be used to store the image processing module 141, the model editing module 142, the model database 143, the medical image data, and model data described in each of the embodiments provided by the invention and allows the processing device 110 to perform reading and execution. In this embodiment, the image processing module 141 and the model editing module 142 are implemented through software and are stored in the storage device 140. Further, the image processing module 141 and the model editing module 142 are integrated into a single piece of software and are executed by the processing device 110 as one software format.

In this embodiment, the output device 150 may be, for example, an automatic modeling device or a 3D printer. The processing device 110 may output edited model data to the output device 150 according to a specific data format (e.g., a 3D printing data format). Hence, the output device 150 may manufacture a physical model object according to the edited model data.

It should be noted that the medical image data described in this embodiment refers to a tomography file conforming to Digital Imaging Communications in Medicine (DICOM), such as computed tomography (CT), magnetic resonance imaging (MRI), and so on. Besides, the medical image data of this embodiment belongs to image data of a biological bone tissue. In this embodiment, the processing device 110 is required to execute one single piece of modeling software only and provides the medical image data and the bone model to the display device 120, and in this way, the display device 120 may simultaneously display the medical image and a 3D bone model in a single window screen of a special operation interface generated by the single piece of modeling software. Further, the medical image modeling system 100 may edit the bone model according to the operational commands provided by the use.

In order to allow people having ordinary skill in the art to further understand the modeling method provided by the invention, description of the modeling method is provided in the following embodiments of FIG. 2 to FIG. 4C.

Figure 2:
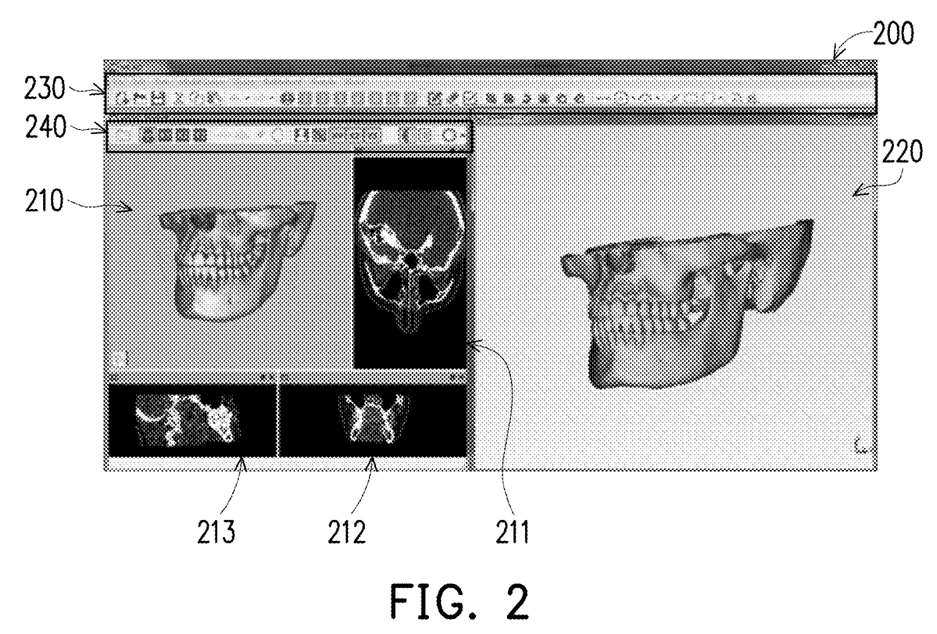
FIG. 2 is a schematic image of an interface of a medical image modeling system according to an embodiment of the invention.
Figure 3A:
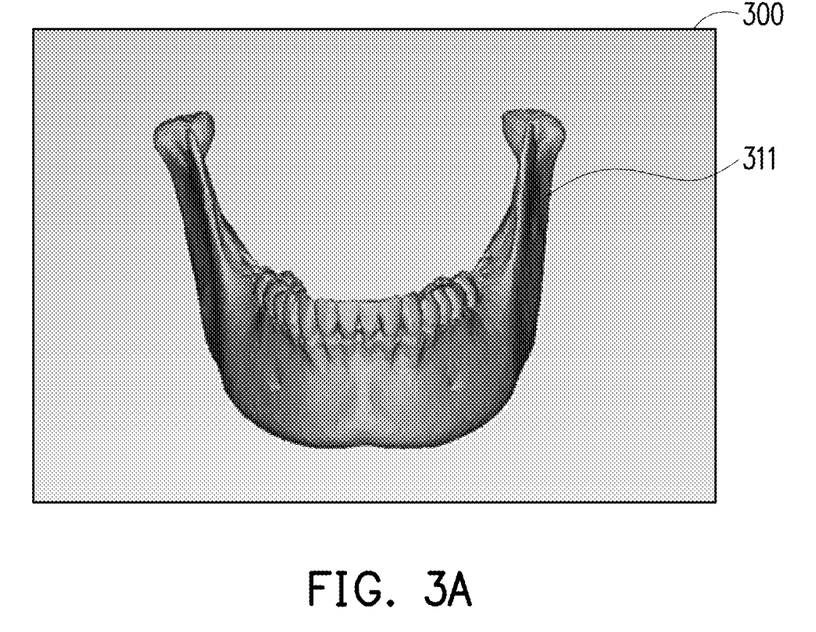
FIG. 3A and FIG. 3B are schematic images of a mandible medical image and a mandible model image according to an embodiment of the invention.
Figure 3B:
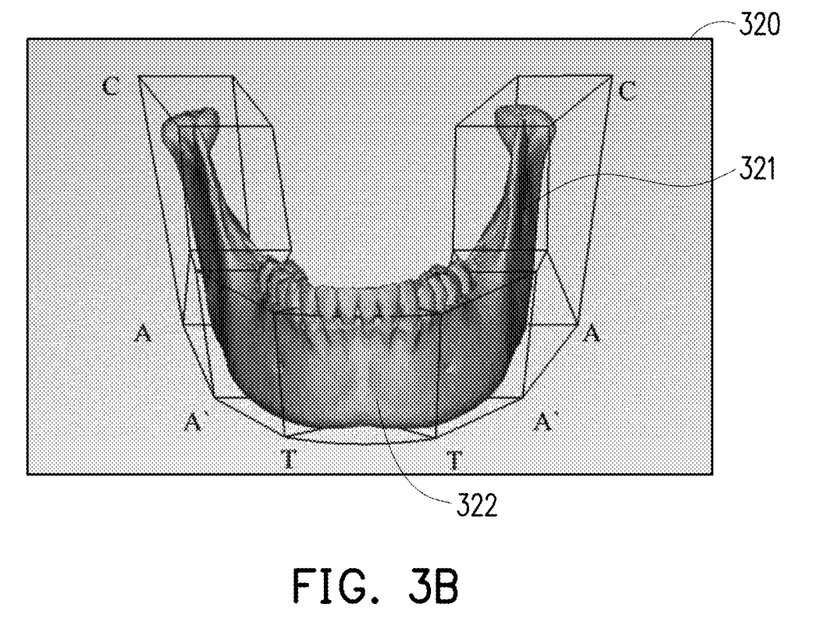

FIG. 2 is a schematic image of an interface of a medical image modeling system according to an embodiment of the invention. FIG. 3A and FIG. 3B are schematic images of a mandible medical image and a mandible model image according to an embodiment of the invention. With reference to FIG. 1 to FIG. 3B, a sub-window of a window in an operation interface 200 displayed by the display device 120 may display a skull medical image 210 as shown in FIG. 2. To be specific, in this embodiment, the user may input a first operational command to the medical image modeling system 100 so that the processing device 110 converts skull medical image data into skull model data in response to the first operational command. In this embodiment, the processing device 110 executes the image processing module 141 in response to the first operational command so as to execute an image processing operation on the medical image data. The image processing operation may include, for example, bone density, size, and angle measurement, layer-slicing browsing, or pixel data extraction operation and the like, and the invention is not limited thereto. Further, in this embodiment, the skull model data conforms to a stereo lithography (STL) format. In addition, the image processing module 141 may convert a 3D image (volumn) formed by stacking multiple layers of two-dimensional medical images (pixle) into 3D mesh data, so as to generate a skull model image 220 displayed in another sub-window in the same window in the operation interface 200. A skull model in the skull model image 220 is a 3D model of a polygonal mesh.

In this embodiment, the operation interface 200 may include a function menu 230, so that the user may select a related file management icon and a related picture drawing function icon and the like, and two sub-windows may be included in one window of the operation interface 200 One of the two sub-windows is configured to display the skull medical image 210, and the other one of the two sub-windows is configured to display the skull model image 220. The sub-window configured to display the skull medical image 210 may further include a function menu 240, so as to allow the user to select a related image view angle icon and a related layer-slicing browsing icon, so as to display, for example, slicing images 211 to 213 corresponding to different directions.

In this embodiment, the processing device 110 executes the image processing module 141 to perform image segmentation on multiple slicing images 211 to 213 in the skull medical image data obtained through tomography, and retains image pixels of the mandible tissue 311 portion by removing image pixels of other tissues. An image processing principle of the image segmentation is to determine whether the pixels in the image belong to the mandible tissue 311 based on Hounsfield unit (HU) values. Then, the image processing module 141 may execute a volume rendering algorithm. The processing device 110 of this embodiment performs 3D reconstruction on the image pixels of the mandible tissue in the slicing images 211 to 213 by executing the volume rendering algorithm. Then, the image processing module 141 may further include a conversion algorithm of a marching cubes algorithm. The processing device 110 of this embodiment converts the mandible medical image 300 that has been three-dimensionally reconstructed into a stereoscopic mandible model 321 that conforms to the stereo lithography format shown in FIG. 3B.

In an embodiment, the user may also import the mandible medical image only such as the mandible medical image shown in FIG. 3A and may correspondingly enable one sub-window of the operation interface 200 to display the mandible medical image 300 as shown in FIG. 3A. The mandible medical image 300 includes the mandible tissue 311. Further, the other sub-window of the operation interface 200 may correspondingly display a mandible model image 320 as shown in FIG. 3B. The mandible model image 320 includes the mandible model 321. For instance, the user may operate the medical image modeling system 100 first to analyze the medical image data, and since an original medical image may include a human body tissue and the bone tissue, the medical image modeling system 100 may first perform bone density, size, and angle measurement on the medical image data, so as to obtain the mandible medical image 300 as shown in FIG. 3A. Next, the user performs layer-slicing browsing on the mandible medical image 300 to evaluate the mandible tissue 311 in the mandible medical image 300. Next, the user may perform pixel data extraction on the mandible medical image 300, so as to generate the mandible model 321 as shown in FIG. 3B. In this embodiment, a defect block 322 required to be repaired may exist on the mandible model 321 (the mandible tissue 311), so the user may perform modeling on the defect block 322 required to be repaired.

Figure 4A:
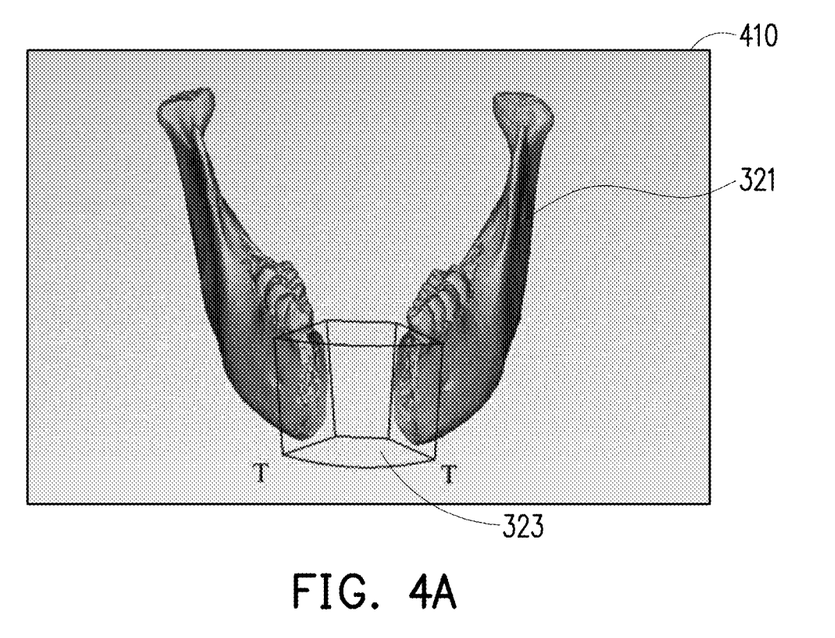
FIG. 4A, FIG. 4B, and FIG. 4C are schematic images of mandible model image editing according to an embodiment of the invention.
Figure 4B:
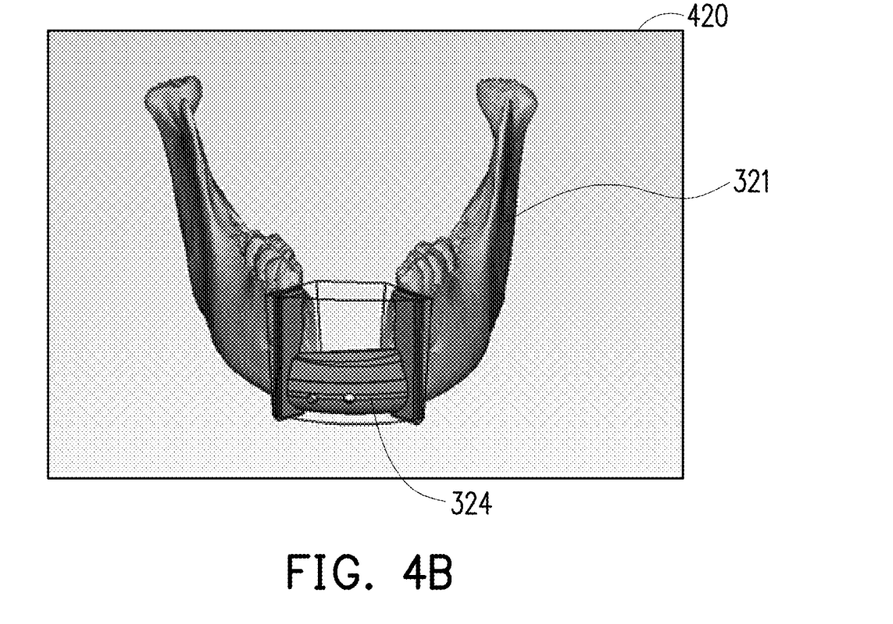
Figure 4C:
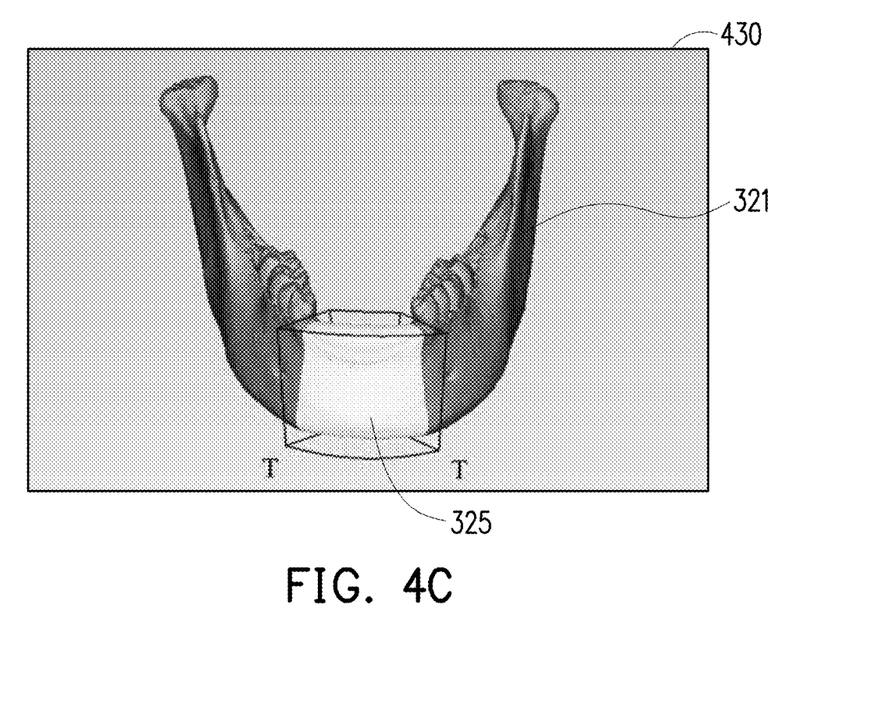

FIG. 4A, FIG. 4B, and FIG. 4C are schematic images of mandible model image editing according to an embodiment of the invention. With reference to FIG. 1 to FIG. 4C, in this embodiment, the medical image modeling system 100 may simultaneously display the mandible medical image of FIG. 3A in the same window of the same operation interface through the display device 120, so in other words, the user is able to see the mandible medical image 300 and the mandible model image 320 at the same time in the display screen of the same operation interface displayed by the display device 120 and may depict and edit the 3D mandible model 321.

With reference to FIG. 4A to FIG. 4C, in this embodiment, the user may determine a specific border position of the defect block 322 on the mandible model 321 in a mandible model image 410 first, and then the user may design a corresponding surgical guide plate model 324 and a bone reconstruction model 325 in an area of the defect block 322 of which the specific border position is determined. As a side note, the surgical guide plate model 324 is configured to perform reference positioning on the defect block 322 in a mandible surgery process, to facilitate correct removal of the defect block 322 performed by the user. Moreover, the mandible model 321 may be similar to the mandible model image 410 shown in FIG. 4A after the defect block 322 is removed.

Specifically, first, the user may input a second operational command to the medical image modeling system 100, so that the processing device 110 reads the model database 143 in response to the second operational command to obtain the bone reconstruction block 323 in the mandible model image 410 as shown FIG. 4A which may correspond to the defect block 322 of FIG. 3B. Next, the user may input a third operational command to the medical image modeling system 100, so as to correspondingly edit or adjust the area of the bone reconstruction block 323 according to the border of the defect block 322 on the mandible model 321. Then, the user may input a fourth operational command to the medical image modeling system 100, so that the processing device 110 may edit or depict the surgical guide plate model 324 in the mandible model image 420 as shown in FIG. 4B which may correspond to the defect block 322 of FIG. 3B in response to the fourth operational command. Alternatively, the processing device 110 may also edit or depict a bone reconstruction model such as the bone reconstruction model 325 in a mandible model image 430 of FIG. 4C which may correspond to the defect block 322 of FIG. 3B in response to the forth operational command. That is, the processing device 110 may perform a corresponding model editing operation based on the area of the bone reconstruction block 323 in the bone model 321 in response to the fourth operational command. Therefore, the medical image modeling system 100 provided by this embodiment features the effect of allowing the user to accurately and quickly depict and edit the surgical guide plate model 324 and the bone reconstruction model 325.

Further, in this embodiment, the user may directly edit surgical guide plate model 324 or the bone reconstruction model 325 in the mandible model 430 after integration in one single window in the operation interface, and the processing device 110 may further generate an edited surgical guide plate model and an edited bone reconstruction model according to an editing result of the surgical guide plate model 324 or the bone reconstruction model 325. In this embodiment, the model editing operation may include, for example, a model generating operation, a model depicting operation, a model editing and modifying operation, a model slicing operation, a model filling operation, or other similar editing functions. Further, after editing of the surgical guide plate model 324 or the bone reconstruction model 325 is completed, the processing device 110 may output the edited bone reconstruction model to the output device 150 according to a specific data format (e.g., a 3D printing data format), so that the output device 150 may continue to manufacture a physical model.

It is worth noting that, in this embodiment, the model editing module 142 may provide a special classification example frame as shown in FIG. 3B. In FIG. 3B, the mandible model 321 may be analyzed and that a plurality of classification icons C, A, A', and T are marked. The user may input a fifth operational command to the medical image modeling system 100 so that the processing device 110 may select at least one of the classification icons of the mandible model 321 in response to the fifth operational command. Further, the processing device 110 correspondingly reads the model database 143 according to a selection result of the classification icons C, A, A', and T, so as to obtain the bone reconstruction block 323 as shown in FIG. 4A. For instance, if the fifth operational command input by the user is selecting a classification icon "TT", it means that a block between the classification icon "T" and the classification icon "T" is selected, so the processing device 110 may correspondingly read the bone reconstruction block 323 of the same block in the model database 143. Nevertheless, in this embodiment, positions and classification manners of the classification icons C, A, A', and T as shown in FIG. 3B are set according to the mandible computed axial tomography (CAT) classification method.

Figure 5:
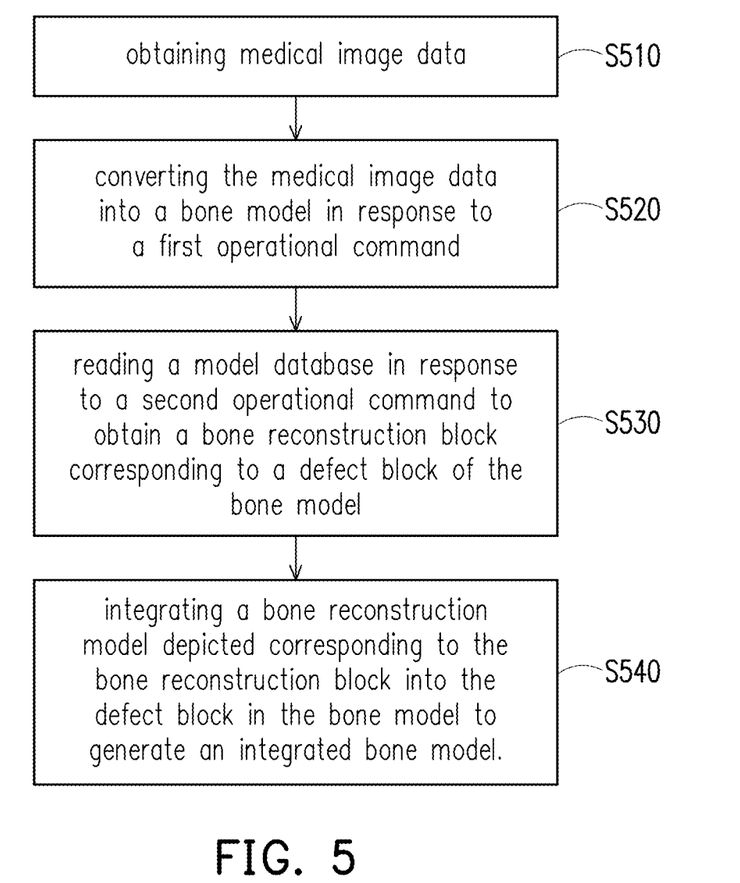
FIG. 5 is a flowchart of a medical image modeling method according to an embodiment of the invention.

FIG. 5 is a flowchart of a medical image modeling method according to an embodiment of the invention. With reference to FIG. 1 and FIG. 5, a medical image modeling method of this embodiment may at least be applied to the medical image modeling system 100 of FIG. 1. The medical image modeling system 100 may perform the following steps S510 to S540. In step S510, the medical image modeling system 100 may obtain the medical image data through the input device 130. In step S520, the processing device 110 of the medical image modeling system 100 converts the medical image data into a bone model in response to a first operational command. In step S530, the processing device 110 of the medical image modeling system 100 reads the model database 143 in response to a second operational command to obtain a bone reconstruction block corresponding to a defect block of the bone model. In step S540, the processing device 110 of the medical image modeling system 100 integrates a bone reconstruction model depicted corresponding to the bone reconstruction block into the defect block in the bone model to generate an integrated bone model. Therefore, the medical image modeling method provided by the invention can provide a fast and convenient bone model modeling function.

Besides, other details of device features, implementation, and techniques of the medical image modeling system 100 of this embodiment can be understood sufficiently from the teaching, suggestion, and illustration of the embodiments of FIG. 1 to FIG. 4 and thus are not repeated hereinafter.

In summary, in the medical image modeling system and the medical image modeling method described in the embodiments of the invention, the bone reconstruction block may be rapidly introduced into the bone model through the model database pre-established in the storage device, and then the surgical guide plate model or the bone reconstruction model may be further edited or depicted within the area of the bone reconstruction block. Further, in the medical image modeling system and the medical image modeling method provided by the embodiments of the invention, the model editing operation can be performed in one single window in one single operation interface according to the operational command inputted by the user. Therefore, by the embodiments of the invention, the medical image modeling system and the medical image modeling method may provide an effective and rapid bone model modeling function, and an appropriate surgical guide plate model or a bone reconstruction model may thereby be effectively produced.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:
1. A medical image modeling system, comprising:
an input circuit, configured to obtain medical image data;
a processor, coupled to the input circuit;
a storage circuit, coupled to the processor, configured to store a model database; and
a display screen, configured to display an operation interface;
wherein the processor, in response to operational commands, causes the system to:

convert the medical image data into a bone model, wherein the converted bone model comprises a plurality of classification icons;

simultaneously display a medical image and a bone model image in a window in the operation interface according to the medical image data and the converted bone model;

select at least one classification icon of the plurality of classification icons of the converted bone model and correspondingly read the model database according to a selection result of the plurality of classification icons to obtain a surgical guide plate model and a bone reconstruction block corresponding to a defect block of the converted bone model;

use the surgical guide plate to perform reference positioning on the defect block to facilitate correct removal of the defect block, wherein the bone reconstruction block is a hollowed space corresponding to region of the removed defect block where a bone reconstruction model is to be integrated into;

place the bone reconstruction block onto the converted bone model according to the region of the removed defect block;

edit an area of the bone reconstruction block in the window in the operation interface according to a border of the defect block; and integrate the bone reconstruction model depicted into the bone reconstruction block to generate an integrated bone model.

2. The medical image modeling system as claimed in claim 1, wherein the processor further causes the system to perform a model editing operation within the area of the bone reconstruction block to depict and edit the bone reconstruction model or the surgical guide plate model.

3. The medical image modeling system as claimed in claim 2, wherein the processor further causes the system to output the edited bone reconstruction model to an output device according to a specific data format so that the output device performs model manufacturing.

4. The medical image modeling system as claimed in claim 1, wherein the processor further causes the system to execute an image processing operation on the medical image data, wherein the image processing operation comprises bone density, size, and angle measurement, layer-slicing browsing, or pixel data extraction operation.

5. The medical image modeling system as claimed in claim 1, wherein the converted bone model is a mandible model.

6. A medical image modeling method, comprising:
obtaining medical image data;
converting the medical image data into a bone model, wherein the converted bone model comprises a plurality of classification icons;
displaying an operation interface and simultaneously displaying a medical image and a bone model image in a window in the operation interface according to the medical image data and the converted bone model;
selecting at least one classification icon of the plurality of classification icons of the converted bone model and correspondingly reading a model database according to a selection result of the plurality of classification icons to obtain a surgical guide plate model and a bone reconstruction block corresponding to a defect block of the converted bone model;
performing reference positioning on the defect block by using the surgical guide plate to facilitate correct removal of the defect block, wherein the bone reconstruction block is a hollowed space corresponding to region of the removed defect block where a bone reconstruction model is to be integrated into;
placing the bone reconstruction block onto the converted bone model according to the region of the removed defect block;
editing an area of the bone reconstruction block in the window in the operation interface according to a border of the defect block; and
integrating the bone reconstruction model depicted into the bone reconstruction block to generate an integrated bone model.

7. The medical image modeling method as claimed in claim 6, further comprising:
performing a model editing operation within the area of the bone reconstruction block to depict and edit the bone reconstruction model or the surgical guide plate model.

8. The medical image modeling method as claimed in claim 7, further comprising:
outputting the edited bone reconstruction model to an output device according to a specific data format so that the output device performs model manufacturing.

9. The medical image modeling method as claimed in claim 6, further comprising:
executing an image processing operation on the medical image data, wherein the image processing operation comprises bone density, size, and angle measurement, layer-slicing browsing, or pixel data extraction operation.

10. The medical image modeling method as claimed in claim 6, wherein the converted bone model is a mandible model.

* * * * *